United States Patent [19]

Alchas et al.

[11] Patent Number: 5,035,708

[45] Date of Patent: Jul. 30, 1991

[54] ENDOTHELIAL CELL PROCUREMENT AND DEPOSITION KIT

[75] Inventors: Paul G. Alchas, Wayne; Frank A. Augello, Cedar Knolls, both of N.J.; Christopher J. Brooks, Glen Cove, N.Y.; Tony A. Cutshall, Boonton, N.J.; Joseph A. DiPisa, Jr., Wyckoff, N.J.; Stuart K. Williams, Wilmington, Del.; Jonathan B. Gabel, Clifton, N.J.; Paul J. Mulhauser, New York, N.Y.; Wes Prais, Hewitt, N.J.; Bruce E. Jarrell, Philadelphia; Deborah G. Rose, Warrington, both of Pa.

[73] Assignees: Thomas Jefferson University, Philadelphia, Pa.; Becton, Franklin Lakes, N.J.

[21] Appl. No.: 356,431

[22] Filed: May 24, 1989

Related U.S. Application Data

[60] Continuation-in-part of Ser. No. 244,496, Sep. 12, 1988, which is a division of Ser. No. 742,086, Jun. 6, 1985, Pat. No. 4,820,626.

[51] Int. Cl.⁵ .................................................. A61F 2/06
[52] U.S. Cl. .......................................... 623/1; 623/12; 623/15; 600/36; 604/35; 604/48; 604/319; 604/902; 435/1; 435/240.21
[58] Field of Search ................. 623/1, 12, 15; 600/36; 604/4, 5, 19, 35, 48, 248, 319, 902; 128/752; 435/1, 240.21, 290; 30/210; 210/258, 217

[56] References Cited

U.S. PATENT DOCUMENTS

| | | | |
|---|---|---|---|
| 3,866,608 | 2/1975 | Reynolds et al. | 604/319 X |
| 4,546,500 | 10/1985 | Bell | 435/1 X |
| 4,753,634 | 6/1988 | Johnson | 604/35 |
| 4,775,365 | 10/1988 | Swartz | 604/248 X |
| 4,795,459 | 1/1989 | Jauregui | 435/1 X |
| 4,815,462 | 3/1989 | Clark | 604/902 X |
| 4,834,703 | 5/1989 | Dubral et al. | 604/48 |

FOREIGN PATENT DOCUMENTS

| | | | |
|---|---|---|---|
| 0158796 | 2/1983 | Fed. Rep. of Germany | 435/240.21 |
| 8401892 | 5/1984 | World Int. Prop. O. | 623/1 |
| 8704935 | 8/1987 | World Int. Prop. O. | 623/1 |

OTHER PUBLICATIONS

Berger et al., "Healing of Arterial Prostheses in Man It's Completeness" Ann. Surg 175:118–127 (1972).

*Primary Examiner*—Randy Citrin Shay
*Attorney, Agent, or Firm*—Woodcock Washburn Kurtz Mackiewicz & Norris

[57] ABSTRACT

The invention is an endothelial cell procurement and deposition kit for collecting fat from a patient, processing said fat to produce an endothelial cell deposition product, and depositing said product on the surface of a graft, all under sterile conditions established and maintained within the components of said kit comprised of: fat collection means for collecting subcutaneous fat from a patient; digestion means connectable to said fat collection means to maintain sterility during reception of said fat and for retaining said fat under sterile conditions during rinsing and digestion to produce a digested product; endothelial cell isolation means connectable to said digestion means for maintaining sterile conditions during reception of said digested product and for separating and isolating microvessel endothelial cells from said digested product to produce an endothelial cell product; cell deposition means connectable to said isolation means for maintaining sterile conditions during reception of said endothelial cell product and for depositing said cells on the surface of a graft to be implanted in a patient and facilitating implantation of said endothelial graft into a patient.

18 Claims, 12 Drawing Sheets

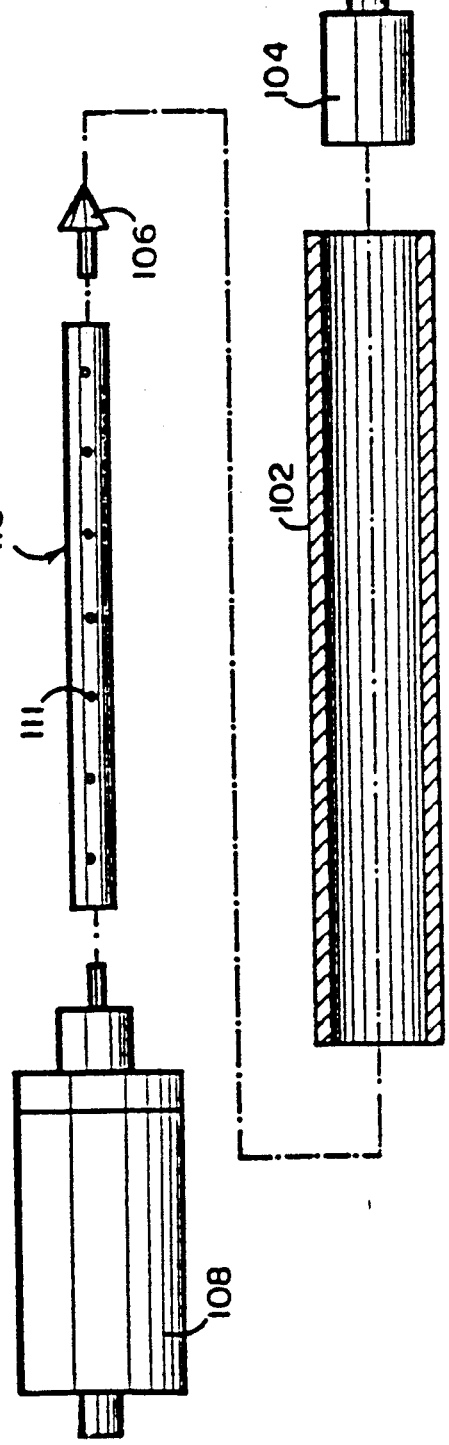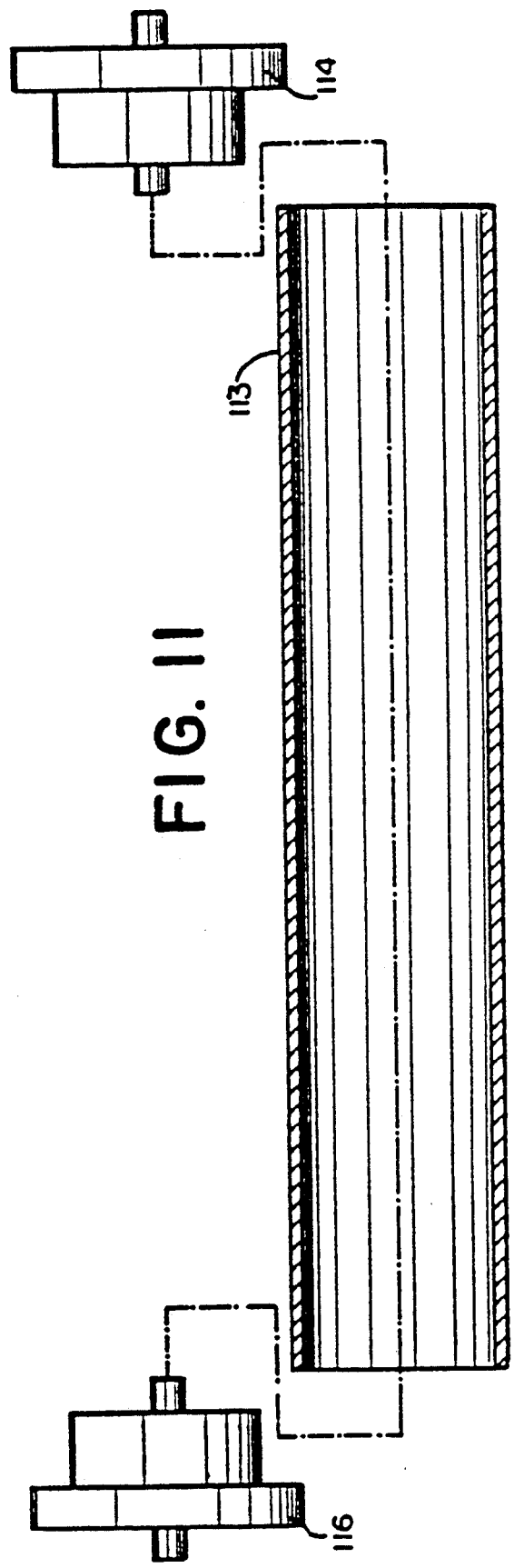

ENDOTHELIAL CELL PROCUREMENT AND DEPOSITION KIT

CROSS-REFERENCE TO RELATED APPLICATIONS

This application is a continuation-in-part of application Ser. No. 244,496, filed Sept. 12, 1988 in the names of Stuart K. Williams and Bruce E. Jarrell entitled "A Method of Treating a Synthetic or Naturally Occurring Surface with Microvascular Endothelial Cells and the Treated Surface Itself", which is a division of application Ser. No. 742,086, filed June 6, 1985 and issued Apr. 11, 1989 as U.S. Pat. No. 4,820,626 in the names of Stuart K. Williams and Bruce E. Jarrell entitled "Method of Treating a Synthetic or Naturally Occurring Surface with Microvascular Endothelial Cells, and the Treated Surface Itself", each of which prior applications is assigned to Thomas Jefferson University, which is a co-assignee with Becton Dickinson and Company of the present application, which applications are hereby incorporated by reference.

This application is related to copending applications Ser. No. 927,745, filed Nov. 6, 1986 entitled "Method of Determining Endothelial Cell Coverage of a Prosthetic Surface"; Ser. No. 848,453, filed Apr. 4, 1986 entitled "A Method of Treating a Synthetic or Naturally Occurring Surface with Collagen Laminate to Support Microvascular Endothelial Cell Growth and the Surface Itself"; Ser. No. 114,242, filed Oct. 28, 1987 now U.S. Pat. No. 4,883,755 entitled "Method of Reendothelializing Vascular Linings", all of which are continuation-in-parts of parent application Ser. No. 742,086, filed June 6, 1985 now U.S. Pat. No. 4,820,626, each of which applications is assigned to Thomas Jefferson University, which applications are hereby incorporated by reference.

BACKGROUND OF THE INVENTION

While autologous vein remains the graft of choice, advanced vascular disease and prior surgical intervention limit the availability of autologous grafts. The use of synthetic grafts provides a means for restoring blood flow to ischemic areas when no alternative is available. Commercially available grafts are far from ideal due to their inherent thrombogenicity. The transplantation of a functional endothelial cell lining onto the surface of a vascular graft has proven to increase patency rates and decrease thrombus formation on the flow surface in animal models. Past and present studies have focused on the isolation of large vessel endothelial cells from vein segments, with the subsequent seeding of these cells on the graft lumenal surface. Tissue culture advances have also made the generation of large numbers of endothelial cells for high-density seeding on vascular prosthesis possible. These techniques have major drawbacks in the clinical setting. Endothelialization occurs at a slow rate when low density seeding techniques are applied. High-density seeding, using cultured endothelial cells requires the use of undefined media, not easily applicable to the clinical setting.

To overcome the problems associated with seeding large vessel endothelial cells on prosthetic grafts, methods for the isolation of microvessel endothelial cells from autologous adipose tissue followed by high density seeding of a vascular prosthesis were developed.

Although microvessel endothelial cells have been shown to be capable of endothelializing a blood-contacting surface, methods of procuring and depositing these cells in an operating room setting present special considerations. Methods currently used employ standard laboratory equipment such as beakers, flasks, centrifuge tubes, shaker baths, pipettes, syringes, sterile hoods. For example, in Williams' and Jarrell's U.S. Pat. No. 4,820,626 and related applications, methods of treating a graft surface with endothelial cells are disclosed. According to those methods, subcutaneous adipose tissue is aspirated via a cannula and transferred by vacuum into a mucous trap. The trap is then transferred to a sterile hood for further processing. Adipose tissue is transferred to a sieve inside a funnel which is placed in a sterile beaker. A rinsing solution is then poured over the tissue to remove red blood cells and lysed fat. The tissue is manually poured into a sterile Erlenmeyer flask containing collagenase solution and agitated at 37° C. for 20 minutes. The collagenase slurry is manually poured into sterile conical centrifuge tubes and spun for seven minutes at 700×G. The endothelial cells are then pipetted out of the tube. A graft is tied to a male luer extension and secured within a tube. The cells are resuspended in serum protein media and drawn into a syringe. Using a needle and a syringe, the cells are forced into the lumen of the graft. The graft is manually rotated for 2 hours.

In spite of these advances, a need still exists for a simple, reliable method of producing endothelial cell coatings on a graft in a operating room setting.

SUMMARY OF THE INVENTION

The present invention provides a simple, reliable kit for producing an endothelialized graft using microvascular endothelial cells harvested from the patient who is to receive that graft. The subject kit is designed to isolate endothelial cells from human fat, to process that fat to produce a cell deposition product, and to deposit that product on the surface of a graft, all under sterile conditions established and maintained within the components of the kit. The kit is a closed system which lessens the likelihood of contamination and reduces the amount of labor required and user error.

Accordingly, a primary object of the present invention is the provision of a kit for producing endothelialized grafts for implantation in humans.

Another object of the present invention is the provision of a system which establishes and maintains sterility of harvested autologous endothelial cells during processing procedures required to produce the implantable endothelialized vascular graft.

These and other objects of the present invention will become apparent from the following, more detailed description and is illustrated in its specific embodiment in the accompanying drawings.

BRIEF DESCRIPTION OF THE DRAWINGS

FIG. 10 is a greatly enlarged side view of the components of the inner process tube of FIG. 9;

FIG. 11 is a greatly enlarged side view of the components of the outer process tube of FIG. 9;

DETAILED DESCRIPTION OF THE INVENTION

In accordance with the preferred methods of the present invention, subcutaneous fat is removed from the patient using modified liposuction techniques and transferred to a self-contained, closed device where the fat can be stored under sterile conditions until needed. The fat is sterilely transferred to a digestion device where it is automatically washed initially to remove red blood cells and other debris, followed by a controlled collagenase digestion for 20 minutes at 37° C. The fat slurry is then transferred to an endothelial cell isolation device, again under sterile conditions, where endothelial cells sediment into an isolation device, allowing automatic retrieval of the isolated endothelial cells. The cell suspension is then sterilely transferred to a processing unit wherein the cells are rapidly filtered onto the graft surface under sterile conditions. The endothelial cell isolation and deposition process requires only about 40 minutes for completion using the kit described herein. Following an incubation period, the graft is ready for implantation into the patient. In paired comparisons between the kit and the methods practiced previously, equivalence and reproducibility in the number of isolated endothelial cells and adherence of the cells to graft surface have been observed. The system yields endothelial cell product in numbers acceptable for subsequent high density seeding (range $5.14 \times 10^6$ to $4.24 \times 10^7$ cells from 50 ccs of fat) and adherence to the graft surface.

The kit deposits cells along the entire length and diameter of the graft consistently, with no significant difference in cell concentration as compared by analysis of variance. Significant advantages of the kit include 1) closed, sterile fluid path; 2) minimal user input; 3) compatibility with an operating room environment; 4) optimization of the conditions to a highly reproducible process from patient to patient.

Figure 1:
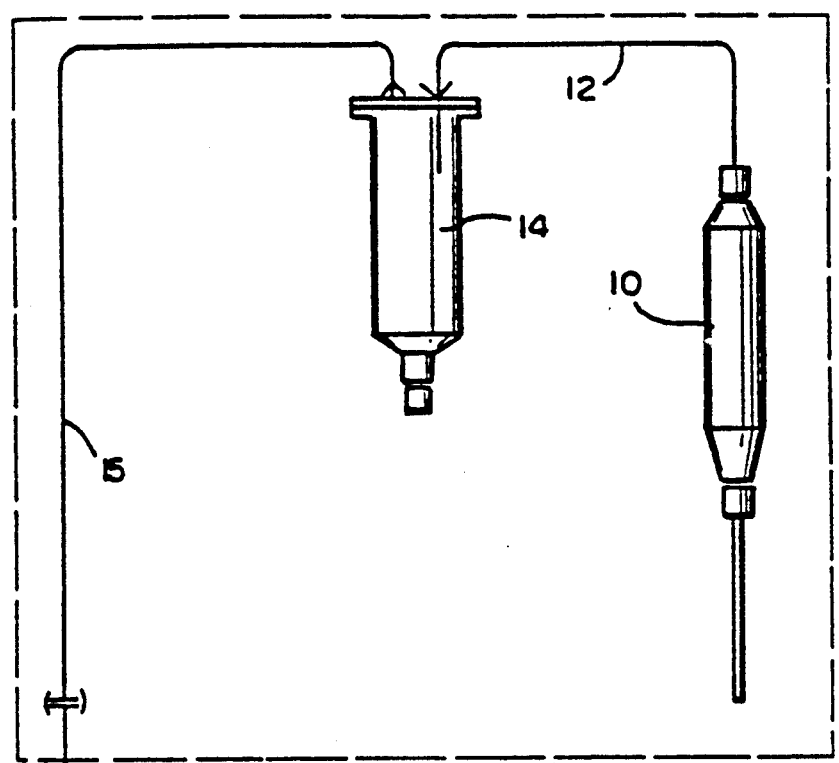
FIG. 1 is a schematic of the fat collection unit which is used to collect fat containing microvascular endothelial cells from the patient to receive the graft, which fat is ultimately collected into a fat collection device.
Figure 3:
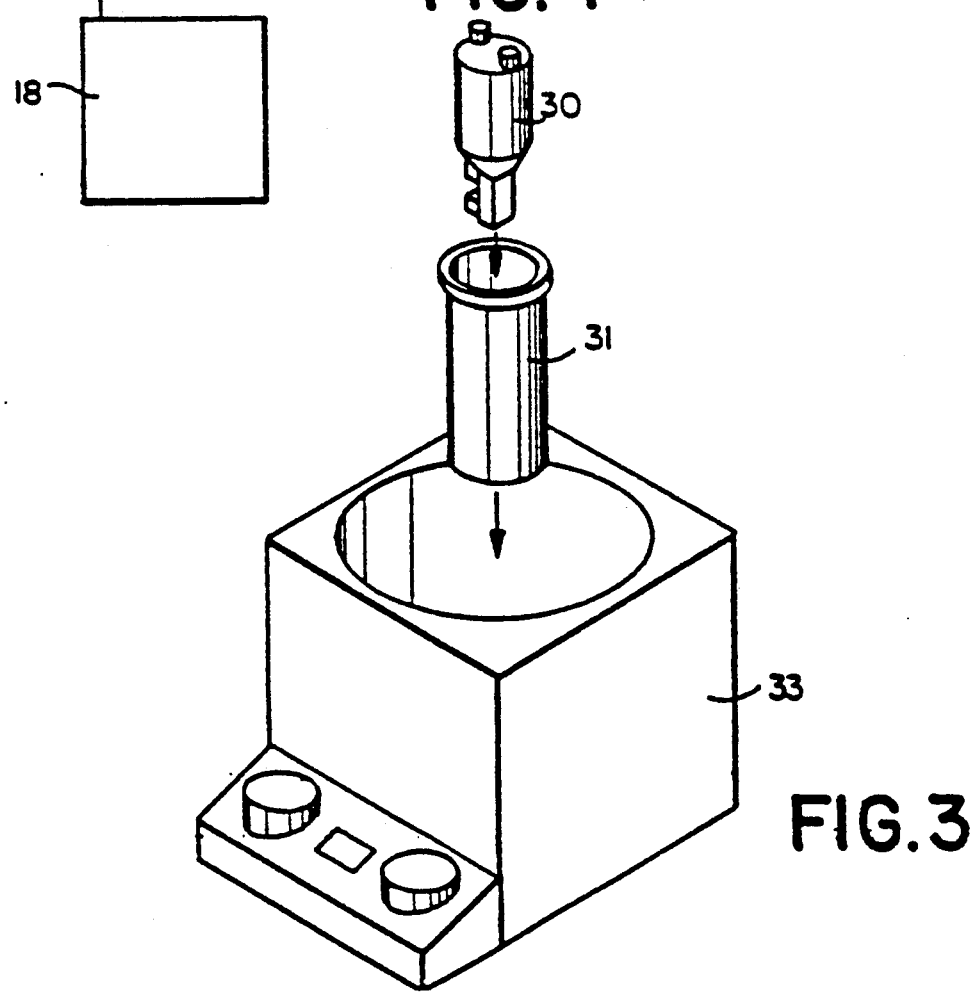
FIG. 3 is a diagram of the endothelial cell isolation unit.
Figure 2:
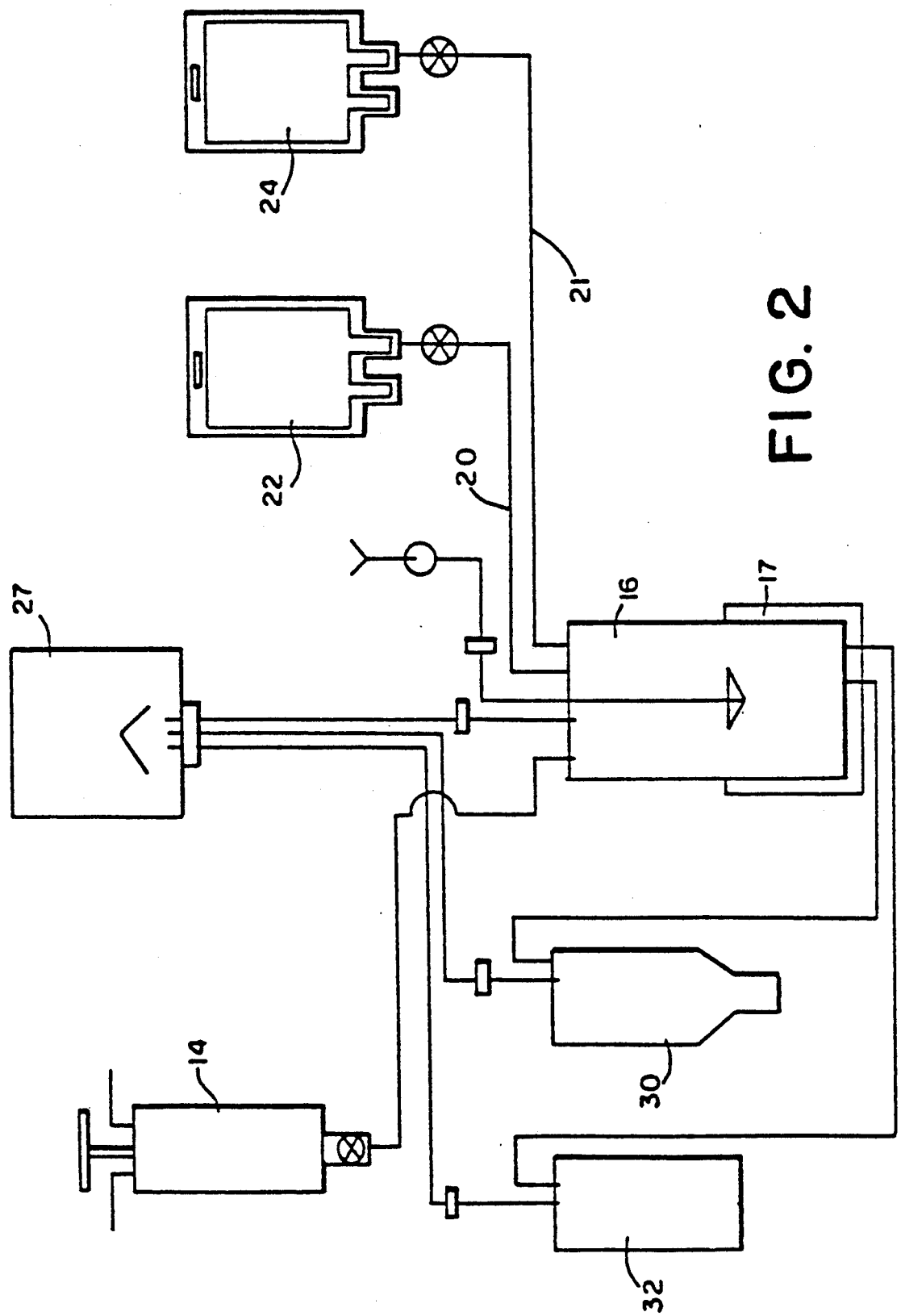
FIG. 2 is a schematic of the digestion unit, wherein the digestion device is shown in association with the fat collection device of the fat collection unit of FIG. 1, which unit is used to produce a digestion product which is transferred to the endothelial cell isolation device, also shown in FIG. 2.
Figure 4:
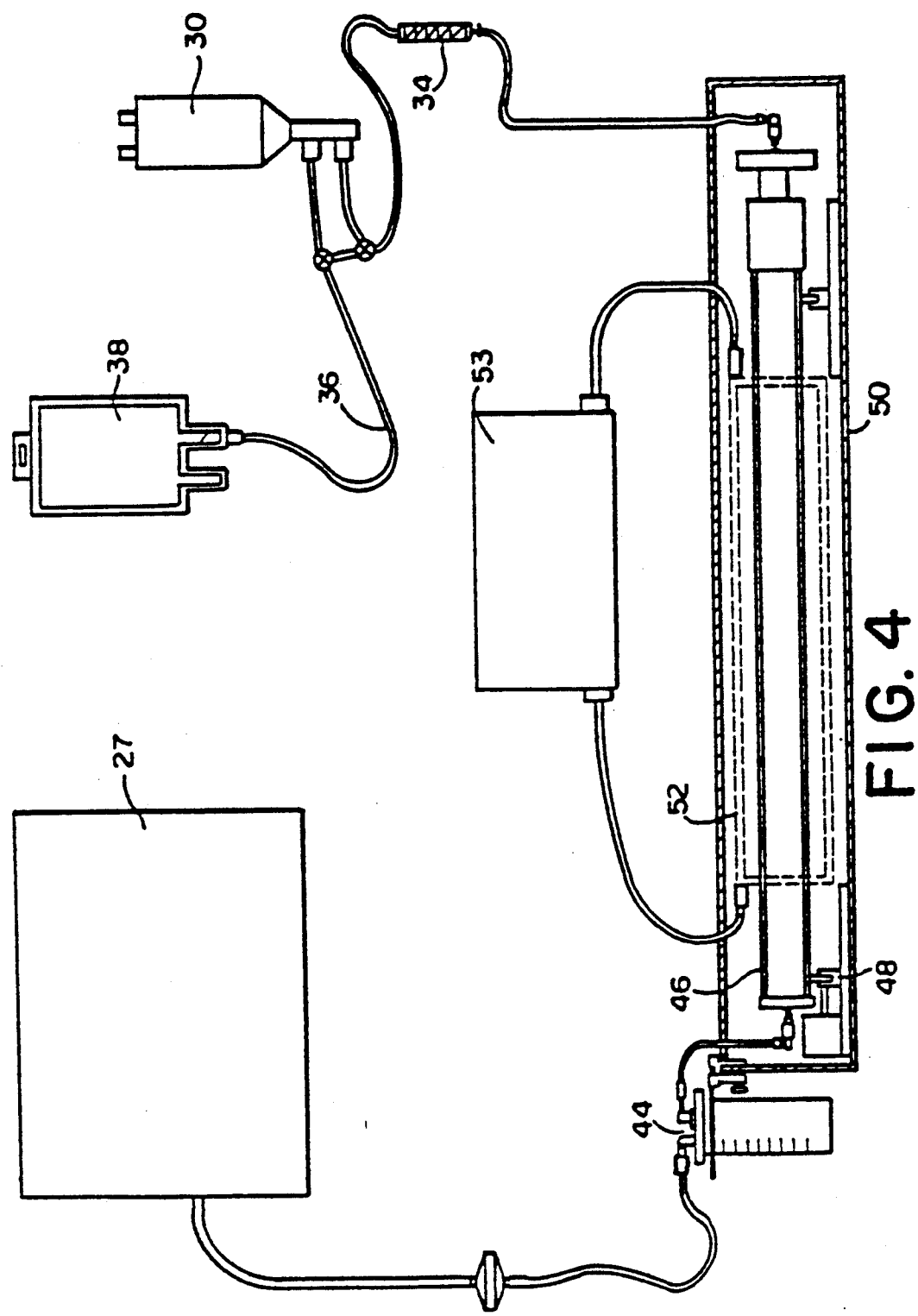
FIG. 4 is a diagram of the vascular graft processing unit and the endothelial cell deposition unit illustrating the components which produce the endothelial cell product and which transfer that product for deposition on a vascular graft.

The system consists of five primary subsystems: 1) fat collection unit (see FIG. 1); 2) digestion unit (see FIG. 2); 3) endothelial cell isolation unit (see FIG. 3); 4) vascular graft processing unit (see FIG. 4); and 5) endothelial cell deposition unit (see FIG. 4).

The fat collection unit (FIG. 1) collects subcutaneous fat tissue sample from a patient. The components include: in-flow tubing (12), fat collection device (14), vacuum tubing (15), aspiration cannula (10) and an aspiration pump (18). The aspiration pump (18) is used to suction subcutaneous fat tissue from the patient through the cannula (10) and in-flow tubing (12) and into the fat collection device (14).

Figure 5:
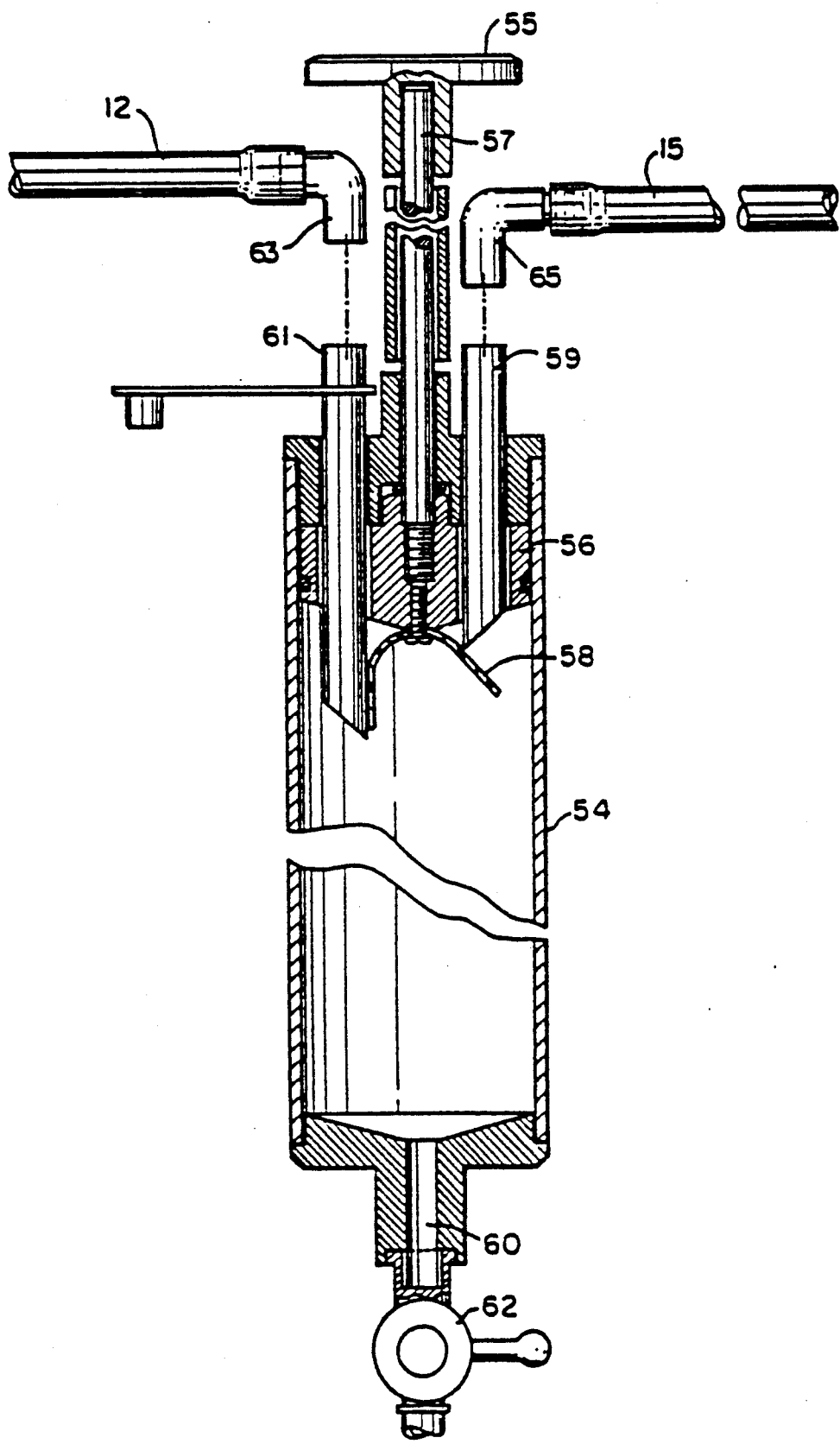
FIG. 5 is a cross-section, on a greatly enlarged scale, of the fat collection device of FIG. 1.

The fat collection device is shown in FIG. 5. It consists of a cylindrical chamber (54) with two vacuum line ports at the top (59 and 61) and an outlet port (60) at the bottom connected to a two-way stopcock (62). A plunger rod (57) passes through the top of the chamber and is connected to a syringe-like stopper (56). The stopper has two holes through which vacuum line ports (59 and 61) pass. When the plunger is in the "down" position, a flexible rubber diaphragm (58) covers the bottom of the stopper and the holes. When the plunger is in the "up" position, the rubber diaphragm (58) is pushed away from the bottom of the stopper by the vacuum line ports (59 and 61), thus opening communication between the inside of the chamber and the vacuum lines (12 and 15). In order to use the device, it must be placed in line with the vacuum line of a liposuction system by using the elbow connectors (63 and 65). In addition, the plunger rod must be in the "up" position. During liposuction, the device acts as a catch trap for the fat tissue. After the appropriate amount of fat is collected, the vacuum line elbow connectors (63 and 65) are disconnected and the plunger rod (57) is pushed down. The rubber diaphragm (58) assumes its original position covering and sealing the bottom of the stopper a it forces the fat tissue out of the outlet port. The subject device serves two functions: to collect fat and facilitate transfer to the digestion unit in a sterile manner.

The digestion unit (FIG. 2) rinses the fat tissue sample with rinse solution and digests it with the enzyme collagenase. The components include: digestion device (16), waste vessel (32) endothelial cell isolation device (30), digestion stand (17), collagenase solution IV bags/sets (20 and 22), rinse solution IV bags/sets (21 and 24), control box (27) for temperature and fluid transfer controls and system vacuum source, assorted tubing connectors, air filters, valves. The fat tissue is manually transferred from the fat collection device (14) through a closed line into the digestion device (16). The fat tissue is rinsed therein with rinse solution introduced into the chamber from the rinse solution IV bags/sets (21 and 24). The rinse solution is drained from the chamber into the waste vessel (32) after rinsing is completed. The collagenase solution is then transferred from the collagenase solution IV bags/sets (20 and 22) into the digestion device (16). Digestion of the fat tissue by the collagenase solution occurs while the mixture is agitated with filtered air and heated to 37° C. The digested fat tissue and collagenase solution mixture is then vacuum transferred into the endothelial cell isolation device (30) for further processing.

Figure 6A:
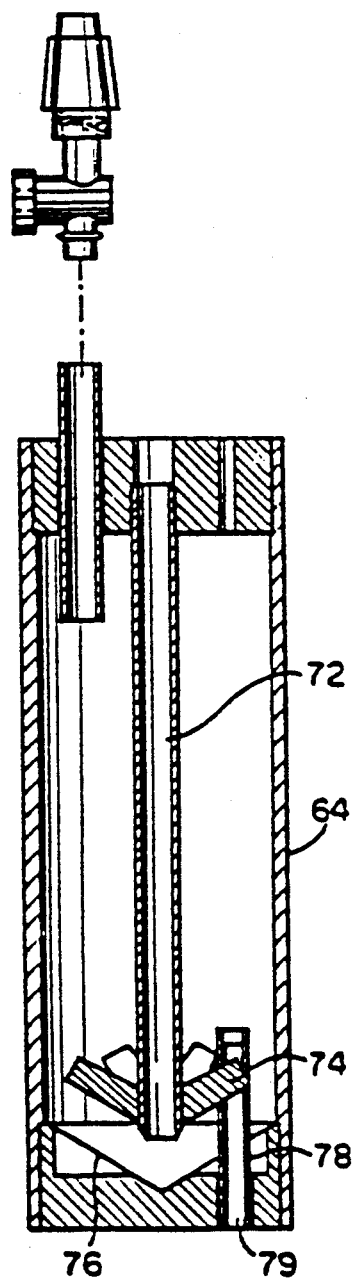
FIG. 6(a) is a longitudinal cross-section, in a greatly enlarged scale, of the digestion device of FIG. 2.
Figure 6B:
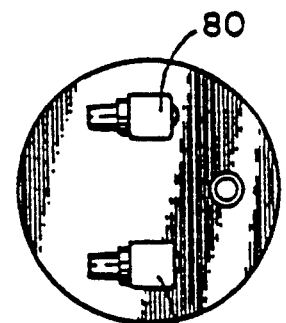
FIG. 6(b) is a bottom view, in a greatly enlarged scale, of the digestion device of FIG. 2.
Figure 6C:
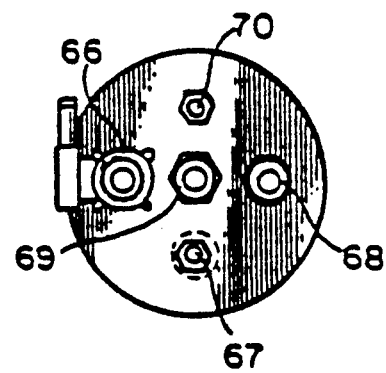
FIG. 6(c) is a top end view, in a greatly enlarged scale of the digestion device of FIG. 2.

The digestion device is shown in FIG. 6. It consists of a chamber (64) with several inlet ports at the top (66, 67, 68, 69 and 70), one of which contains a filter and is connected to a tube (72) which terminates near the bottom of the chamber. A series of "fingers" (74) is bonded to the end of the tube in a radial fashion. At the bottom of the chamber is a conical mesh filter (76) below which are two outlet ports (80 and 82) and a temperature probe sheath (78). During use, the collected fat tissue is introduced into the chamber (64) through one of the top inlet ports (66) followed by rinse solution (Media 199E, Hanks, saline, PBS or other physiological buffered solution) through another of the inlet ports (67). A vacuum line, connected to another inlet port (68) causes filtered air to enter through the center port (69) and tube (72) which air bubbles up through the fat mixture creating agitation. The "fingers"0 (74) serve to distribute the bubbling air to ensure uniform agitation and provide a frictional surface to facilitate break-up of the fat. The rinse solution is then drawn out through the bottom of the mesh and expelled through one of the outlet ports (80) leaving behind fat tissue relatively free of blood. Digestive enzyme solution (collagenase, dispase, trypsin, or other tissue dissociation enzyme) is introduced through another of the top inlet ports (70) followed by agitation by bubbling. Throughout this process, a temperature probe (79) inside the probe sheath (78) monitors the process temperature and sends feedback to an external heat controller within the control box (27). When digestion is complete, the digested fat solution, rich in microvessel endothelial cells, is drawn out through the bottom mesh and expelled through an outlet port (82) for subsequent processing. The mesh (76) retains undigested tissue and large fibrous matter which is discarded with the device. The subject device is a closed system which lessens the likelihood of contamination and reduces the amount of labor and user error.

The endothelial cell isolation unit (shown in FIG. 3) separate and isolates the endothelial cells from within the digested fat tissue sample. The components include: centrifuge (33), centrifuge shields (31), endothelial cell isolation device (30). The endothelial cell isolation device (30) is placed into a centrifuge shield and the assembly is placed into the centrifuge (33). Centrifugation isolates the endothelial cells. The endothelial cell isolation device (30) is then placed in line with the vascular graft processing unit and mounted on the endothelial cell deposition unit.

Figure 7A:
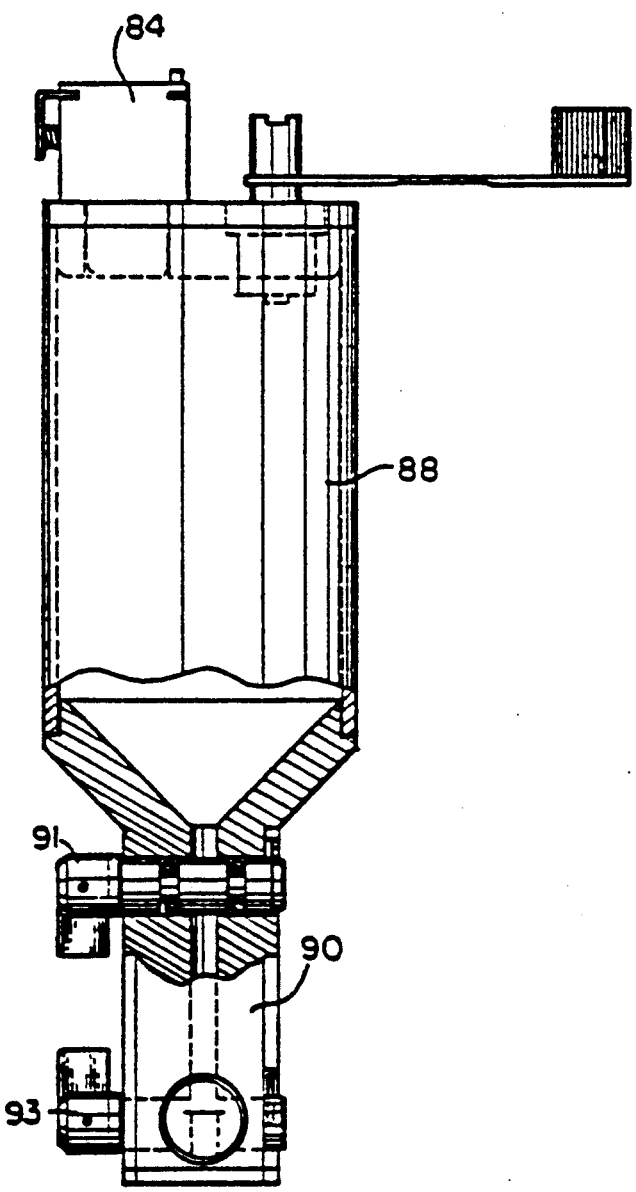
FIG. 7(a) is an enlarged front view of the endothelial cell isolation device of FIG. 2.
Figure 7B:
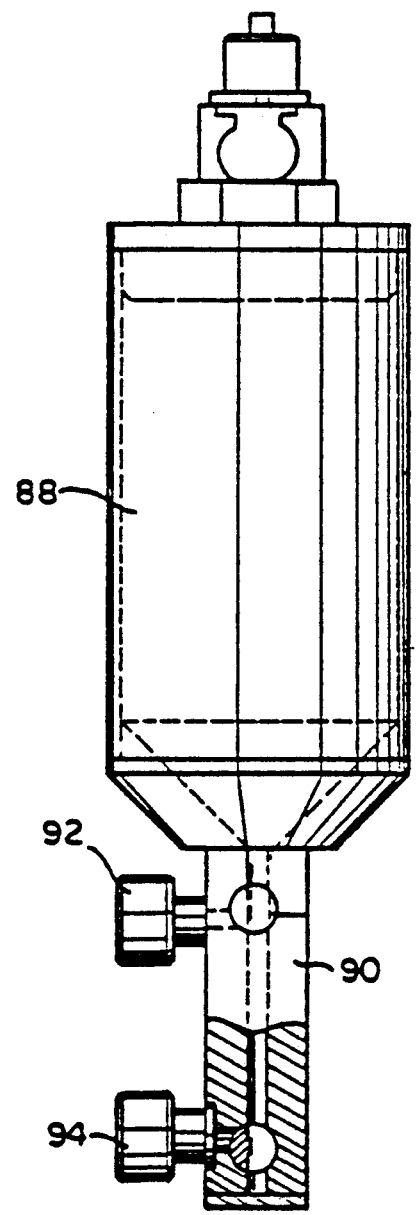
FIG. 7(b) is an enlarged side view of the endothelial cell isolation device of FIG. 2.

The endothelial cell isolation device is shown in FIG. 7. It consists of a primary chamber (88) tapering to a secondary chamber or ampule (90) having inlet and outlet ports (92 and 94). In line with each port (92 and 94) is a two-position valve (91 and 93). The first position allows communication between the primary and secondary chambers. The second position allows communication between the secondary chamber and the outside port. Each valve (91 and 93) is initially turned to the first position. Digested fat tissue is introduced through the top port (84). The device is then placed into a centrifuge and spun. Centrifugation separates endothelial cells into the ampule (90), the dimensions of which are optimized for isolating a "pellet" of endothelial cells between the two ports. The valves are then turned to the second position isolating the "pellet" from the primary chamber (88) above and packed red blood cells below. The endothelial cell "pellet" may then be flushed out by attaching a pressurized line to the inlet port (92) or vacuum line to the outlet port (94). The subject device is a closed system which maintains sterility and reduces the amount of labor and user error.

The vascular graft processing unit shown in FIG. 4 protects, maintains sterility and facilitates the processing of the graft during handling, pre-wetting and cell deposition. The components include: process tube assembly including an inner and an outer tube (46), graft, vacuum line/trap assembly (44), vortex/mesh assembly (34), autologous serum/media solution IV bags/sets (36 and 38). The graft is mounted within the inner tube of the process tube assembly. The purpose of the outer tube is to maintain sterility of the inner tube. The graft is pre-wetted prior to cell deposition by drawing the autologous serum/media solution from an IV bag, through the vortex/mesh assembly, into the lumen of the graft, and out through the graft wall until all air is purged from the inner tube of the process tube assembly. The graft processing unit is then transferred to the endothelial cell deposition unit.

Figure 8:
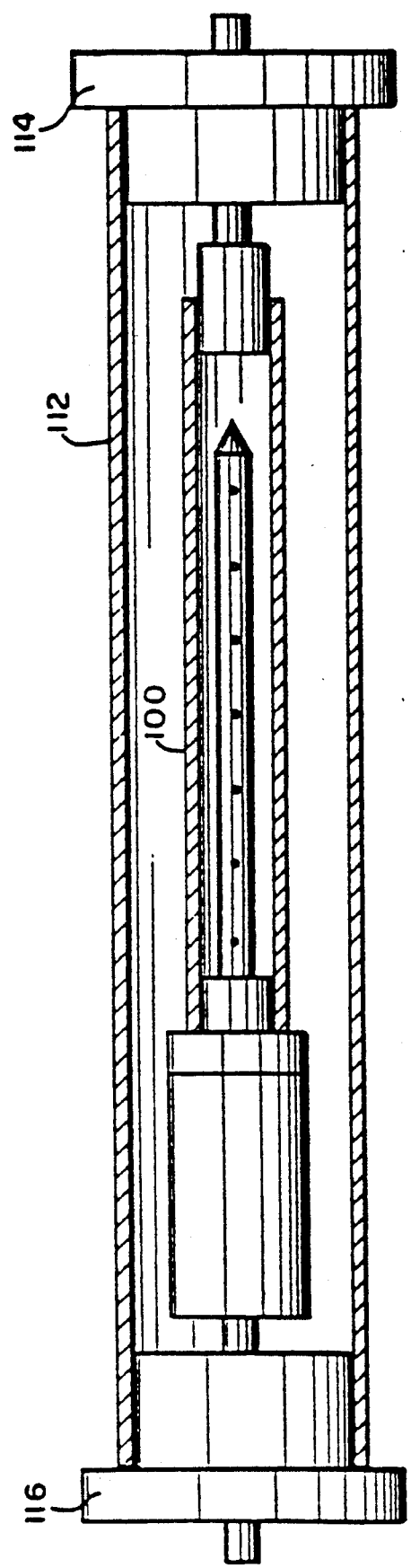
FIG. 8 is a diagrammatic cross section of the process tube assembly, shown in FIG. 4 within the endothelial cell deposition unit which process tube assembly is used to introduce the endothelial cell product onto the interior surface of the graft lumen.
Figure 9:
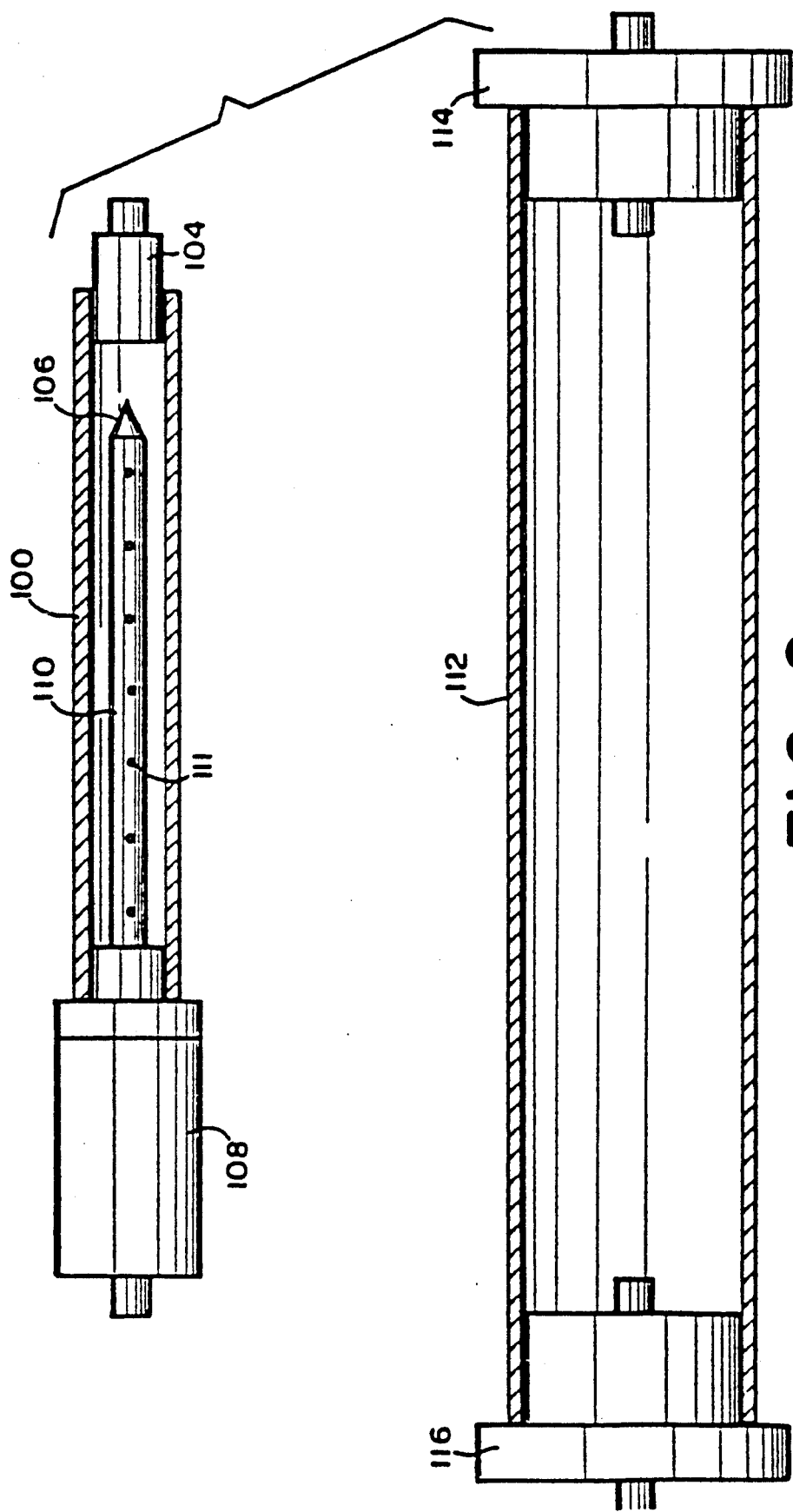
FIG. 9 is an enlarged diagrammatic cross-section of the inner and outer process tubes of the vascular graft processing unit illustrated in FIG. 8.

The fully assembled process tube is shown in FIG. 8. It consists of two major assemblies: inner process tube (100) and outer process tube (112) (see FIG. 9). As shown in FIG. 10, the inner process tube consists of the following sub-assemblies: vent cap (104), handle cap (108), inner process tube body (102), tunneler (110), tunneler tip (106). A graft is threaded through the lumen of the tunneler (110) and is attached to the handle cap (108) prior to assembly. As shown in FIG. 11, the outer process tube consists of the following subassemblies: outer process tube body (113), inflow endcap (116), outflow endcap (114). In its fully assembled form, the process tube assembly serves the following functions: it houses, protects and maintains sterility of the graft during shipment and handling in the operating room; it supports the graft and allows fluid access to the graft lumen during endothelialization; it breaks down into a sub-assembly which facilitates implantation of the graft while protecting the endothelial lining. During endothelialization, the inflow endcap of the device (116) is connected to a container of endothelial cell suspension, and the outflow endcap (114) is connected to a vacuum source in the control box (27). Negative pressure external to the porous graft causes the endothelial cell suspension to flow into the graft lumen and out through the wall thereby filtering endothelial cells onto the inner graft wall. The filtered solution continues to flow out through the holes (111) in the tunneler wall (110) and out of the vent cap (104). During this operation, the device may be rotated about its central axis by the addition of rotary fittings at the outer process tube end caps. After endothelialization is complete, the inner process tube (100) is removed from the outer process tube (112) and the handle cap (108)/tunneler (110)/tip (106) assembly is removed from the inner process tube body (102). The graft may then be "tunneled" through, for example, the patient's leg tissue for proper graft placement without contacting or disturbing the graft. Once positioned, the handle cap (108) is detached from the tunneler (110) and the tunneler (110) is withdrawn, leaving the graft in place for the distal anastomosis. An IV line containing autologous serum media solution may be connected to the handle cap (108) to maintain wetting of the graft lumen during surgical placement. When the distal anastomosis is completed, the graft is snipped at the proximal end, releasing it from the handle cap (108) and readying it for the proximal anastomosis.

The endothelial cell deposition unit shown in FIG. 4 promotes endothelial cell deposition onto the lumen of the graft. The components include: process tube rotation fixture (48), insulated trough (50), heating pad (52), water circulator/heater (53). The process tube assembly (46) is positioned on the rotation fixture within the insulated trough and wrapped in the heating pad which is heated by the water circulator. The cell deposition procedure is initiated by using vacuum to draw autologous serum/media solution and the isolated endothelial cells from endothelial cell isolation device (30). The endothelial cells and autologous serum/media solution pass through the vortex/mesh assembly (34) which breaks up the endothelial cell pellet and filters out gross particulate. The endothelial cells resuspended in the solution are pressurized into the lumen of the graft. The graft filters the solution leaving endothelial cells on the luminal wall. During pressurization, and subsequent cell-graft association, the graft is rotated about its central axis at a constant rate and maintained at 37° C.

Ancillary items include: blood collection bag and transfer bag without anticoagulant to be used for blood collection and serum separation, the serum to be used for the make-up of autologous serum/media solution and an additional solution IV bag filled with autologous serum/media solution and an administration set to be used to maintain the cells during graft implantation.

EXAMPLE 1

Figure 12:
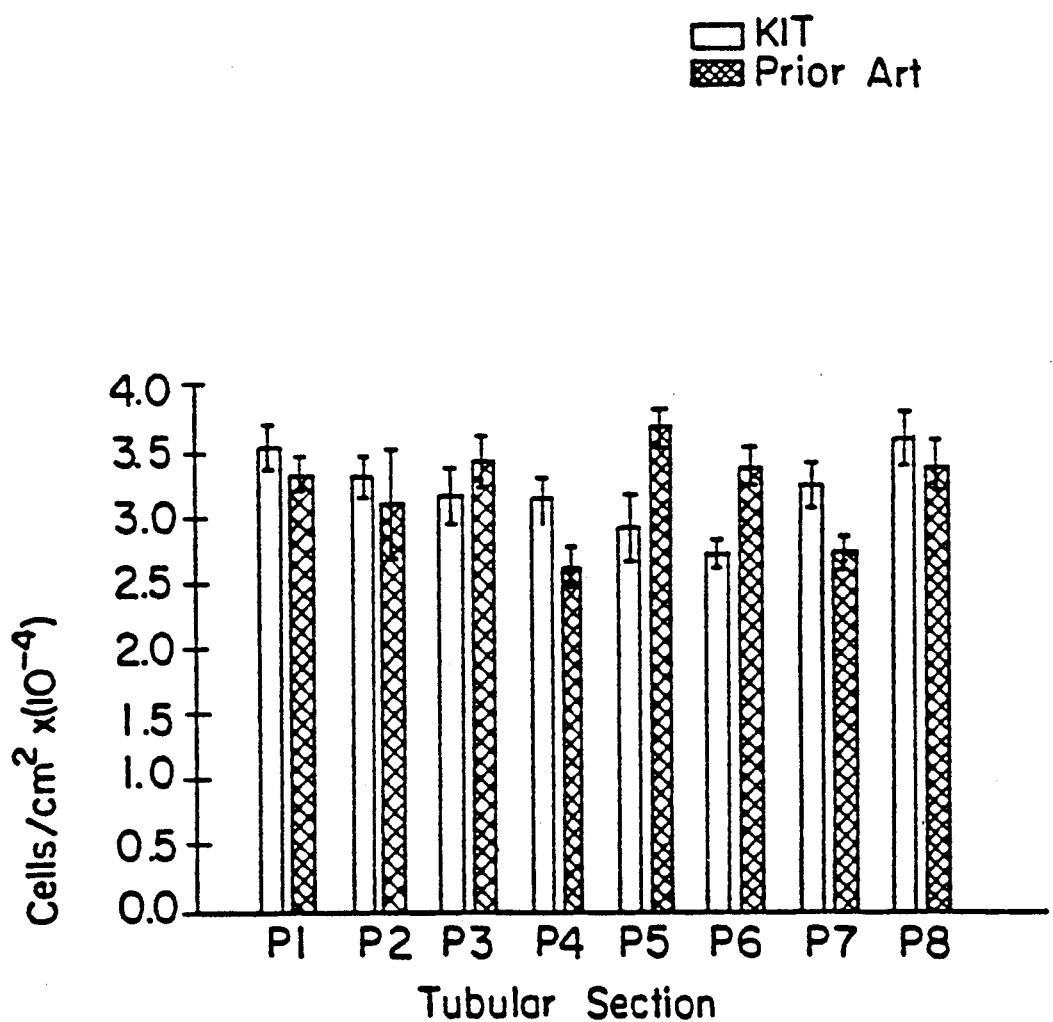
FIG. 12 is a bar graph showing the average endothelial cell density achieved per section of processed graft for the grafts processed using the preferred kit of the present invention and those using prior art methods.

Microvascular endothelial cells were isolated and deposited on 4 mm × 80 cm expanded polytetrafluoroethylene (ePTFE) grafts using both the kit and patented methods. After a two hour rotation, the grafts were rinsed with media and cut into 8 sections. P1 is where the cells were introduced and P8 is the opposite end. The graft segments were hematoxylin stained and the cells counted using an automated image analysis system. FIG. 12 provides the average cell density achieved per section on such Gore-Tex ® tubular grafts.

EXAMPLE 2

Figure 13:
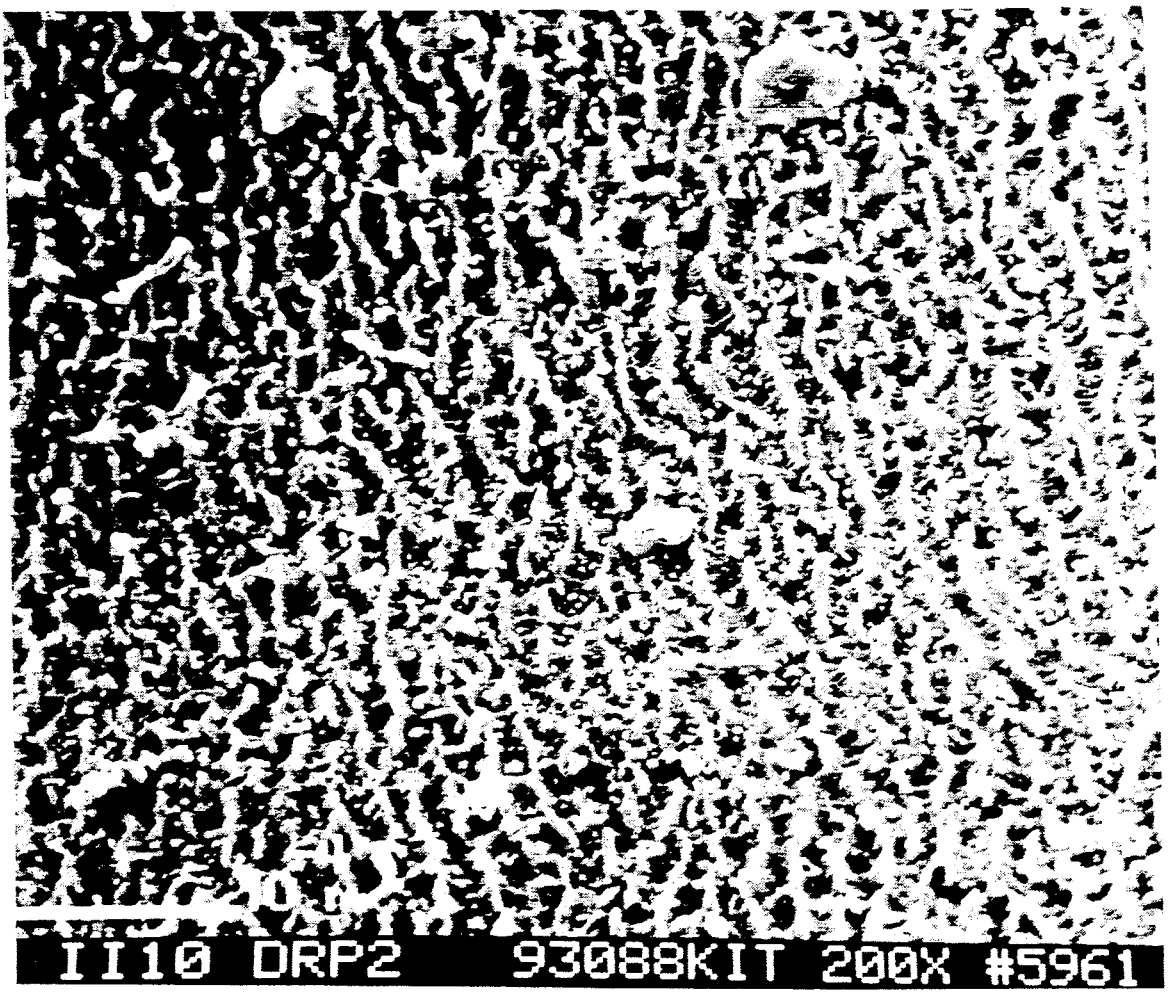
FIG. 13 is a scanning electron micrograph of a graft processed with the preferred kit of the present invention.
Figure 14:
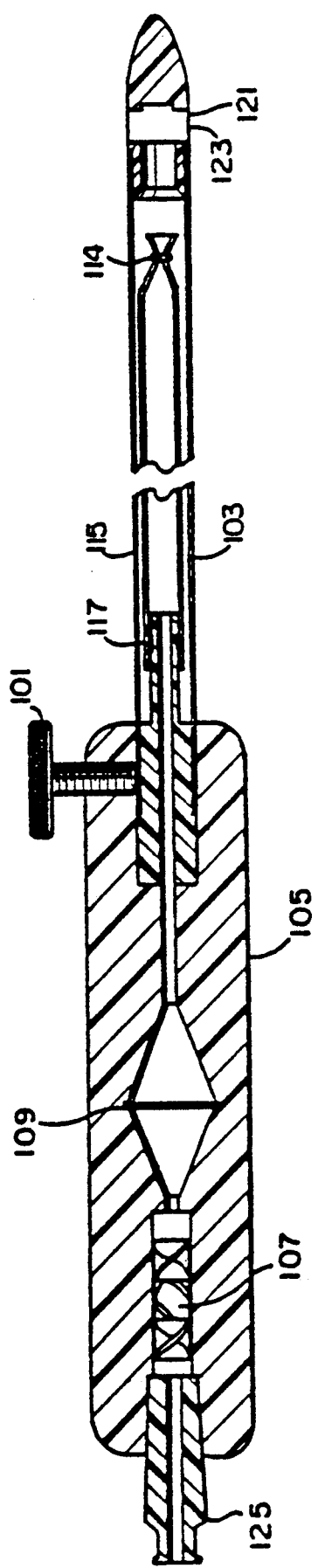

Endothelial cell product was prepared and deposited on an ePTFE graft using the kit. A scanning electron micrograph of the microvascular endothelial cells deposited on the graft is shown in FIG. 13. The endothelial cell product was consistently deposited along the entire length of the graft with no significant variation in cell concentration.

As seen from the above a simple, reliable kit for producing an endothelialized graft using microvascular endothelial cells is provided. These cells are harvested from a patient who is to receive the graft and processed through the use of kit which isolates those cells to produce cell deposition product, and deposits that product on the surface of a graft, all under sterile conditions established and maintained within the components of the kit.

While the foregoing description has been directed to the preferred embodiment kit of the present invention, those of ordinary skill in the art in this field will appreciate that various modifications can be made in the materials and methods described herein without departing from the scope of the present invention, which is defined more particularly in the claims appended hereto.

What is claimed:

1. An endothelial cell procurement and deposition kit for collecting fat from a patient, processing said fat to produce an endothelial cell deposition product, and depositing said product on the surface of a graft, all under sterile conditions established and maintained within the components of said kit, comprising:
   a fat collection means for collecting fat from a patient;
   digestion means connectable to said fat collection means to maintain sterility during reception of said fat and for retaining said fat under sterile conditions during rinsing and digestion to produce a digested product;
   endothelial cell isolation means connectable to said digestion means for maintaining sterile conditions during reception of said digested product and for separating and isolating microvessel endothelial cells from said digested product to produce an endothelial cell product; and
   cell deposition means connectable to said isolation means for maintaining sterile conditions during reception of said endothelial cell product and for depositing said cells on the surface of a graft to be implanted in a patient and facilitating implantation of said endothelialized graft into a patient.

2. The kit of claim 1 wherein said fat collection means further comprises fat receiving means connectable to said fat collection means for receiving said collected fat and for storing said fat under sterile conditions until needed.

3. The kit of claim 2 wherein said fat receiving means further comprises:
   a chamber having a top and a bottom;
   stopper means substantially in a sealing engagement with the chamber capable of being slidably raised and lowered with said chamber;
   inlet tube means connectable to fat collection means extending through said stopper means into said chamber;
   vacuum inlet tube means extending through said stopper means into said chamber;
   plunger means connected to said stopper means for lowering and raising said stopper means;
   diaphragm means affixed to said stopper means for sealing said chamber during fat transfer, said diaphragm means being deflected by said inlet tube means and said vacuum inlet tube means when said stopper means is in a raised position and closing off both said inlet means when the stopper means is in a lowered position thereby facilitating fat transfer from the chamber;
   outlet means affixed to the bottom of the chamber including a valve means for regulating the transfer of fat from the chamber 4. The kit of claim 1 wherein said fat collection means comprises liposuction means.

5. The kit of claim 1 wherein said digestion means further comprises:
   a chamber having a top and a bottom;
   a first inlet port affixed at the top of the chamber connectable to the fat collection means for introducing collected fat into the digestion means chamber;
   a second inlet port affixed at the top of the chamber for introducing rinsing solution into the digestion means chamber;

a third inlet port affixed at the top of the chamber for introducing digesting solution into the digestion means chamber;

a fourth inlet port affixed at the top of the chamber connectable to a vacuum source;

a fifth inlet port affixed at the top of the chamber for introducing filtered ambient air into the digestion means chamber;

a tube centrally disposed within the chamber parallel to the longitudinal axis of the chamber said tube having a top and a bottom, and connected at its top end to said fifth inlet port and connected at its bottom end to an agitating means, through which tube filtered ambient air can be introduced into said chamber;

agitating means connected to the said bottom end of said central tube;

filtering means connectable under the agitating means for retaining undigested debris;

monitoring means connectable at the bottom of the chamber for monitoring the reaction within the chamber;

a first outlet port affixed at the bottom of the chamber for removing rinse solution and digestion debris;

a second outlet port affixed at the bottom of the chamber connectable to the endothelial cell isolation means for transferring said digested product to the endothelial cell isolation means.

6. The kit of claim 5 wherein said monitoring means further comprises:

a protective sheath containing a temperature probe connectable to an external heat controller whereby the reaction temperature within the digestion means is controlled.

7. The kit of claim 5 wherein said agitating means further comprises:

a plurality of elongated members affixed to the centrally disposed tube whereby filtered air introduced through the tube is distributed for uniform agitation and a frictional surface to facilitate fat digestion is provided.

8. The kit of claim 1 wherein said endothelial cell isolation means comprises:

a first chamber connectable to the digestion means for receiving digested product having a top and a bottom;

a first inlet port at the top of said first chamber connectable to the digestion means;

a second chamber connected to the bottom of the first chamber to isolate the endothelial cell product;

a second inlet port affixed to said second chamber having a two-position valve allowing communication between said first and second chamber when in a first position and communication between said second chamber and said inlet port to isolate endothelial cell product when in a second position;

an outlet port affixed to said second chamber having a second two-position valve allowing communication with the portion of said second chamber above said second two-position valve and the portion of said second chamber below said second two position valve to isolate isolated endothelial cell product from packed red blood cells when in a second, closed position;

whereby when said isolation means containing said digested product is centrifuged, the endothelial cells are isolated from the digested product within said second chamber when both of said two position valves are in a second, closed position.

9. The kit of claim 1 wherein said cell deposition means comprises:

an inner process tube for supporting the graft during deposition of endothelial cell product onto the graft under sterile conditions; and an outer process tube for housing the inner process tube, and maintaining sterility during the cell deposition process.

10. The cell deposition means of claim 9 wherein said outer process tube further comprises:

a tube body;

an endcap connectable to the tube body having an inlet means connectable to the endothelial cell isolation means and a communicating outlet means connectable to the inlet means of the inner process tube;

an endcap connectable to the tube body having communicating inlet and outlet means wherein said inlet means is connectable to the outlet means of the inner process tube.

11. The cell deposition means of claim 10 wherein said outer process tube further comprises:

rotary fittings connectable to both end caps whereby the device may be rotated about its central axis.

12. The cell deposition means of claim 9 wherein said inner process tube further comprises:

a tube body;

a tunneler assembly connectable to the tube body and to the outer process tube at the end which is connectable to the cell isolation means;

a vent cap connectable to the tube body having an outlet means connectable to the outer process tube end cap; whereby cell product introduced under pressure flows through the graft housed in the tunneler assembly and deposits cell product onto the graft.

13. The inner process tube of claim 12 wherein the tunneler assembly housing the graft comprises:

a tunneler for supporting the graft;

a tunneler tip connectable to the tunneler for facilitating proper graft placement within the patient;

a handling cap connectable to the tunneler, and to the graft housed within the tunneler, and to the inner process tube body to facilitate handling of the tunneler assembly.

14. The inner process tube of claim 13 wherein said tunneler further comprises:

a tube having a plurality of holes disposed along its axis whereby endothelial cell product flows through the graft housed within the tunneler and then out through said holes depositing endothelial cell product onto the graft.

15. A method for sterilely procuring and depositing endothelial cells onto a graft to be implanted in a patient, said method comprising the steps of:

providing a kit for collecting fat from a patient, processing said fat to produce an endothelial cell deposition product, and depositing said product on the surface of a graft, all under sterile conditions established and maintained within the components of said kit including a fat collection means for collecting fat from a patient, a digestion means for producing a digested product, an endothelial cell means for producing an endothelial cell product and a cell deposition means for depositing said endothelial cell product on said graft;

collecting fat from a patient into said sterile fat collection means;
sterilely transferring said collected fat into said sterile digestion means;
rinsing and digesting said fat within said digestion means to produce a digested product;
sterilely transferring said digested product into said sterile isolation means;
isolating endothelial cells from said digested product within said isolation means to produce an endothelial cell product;
sterilely transferring said endothelial cell product into said sterile cell deposition means; and
sterilely depositing said cell product onto the surface of the graft to be implanted into a patient.

16. The method of claim 15 wherein the step of isolating endothelial cells from digested product further comprises centrifuging said isolation means to isolate said endothelial cell product.

17. The method of claim 15 wherein the step of depositing endothelial cell product onto a graft further comprises:
creating negative pressure external to the graft wherein said graft is porous; and
flowing endothelial cell product into the graft lumen thereby depositing cell product onto the graft surface.

18. The method of claim 17 wherein the method of depositing endothelial cell product onto the surface of the graft further comprises rotating the graft during the cell deposition process.

* * * * *